United States Patent [19]

Shaw

[11] Patent Number: 5,080,864
[45] Date of Patent: Jan. 14, 1992

[54] STOPPER DETECTOR
[75] Inventor: James D. Shaw, Hilton, N.Y.
[73] Assignee: Eastman Kodak Company, Rochester, N.Y.
[21] Appl. No.: 556,671
[22] Filed: Jul. 20, 1990
[51] Int. Cl.5 .......................................... G01N 21/00
[52] U.S. Cl. ....................................... 422/62; 422/63; 422/99; 436/43; 436/47; 436/48; 340/568; 53/505; 53/506
[58] Field of Search ............................ 422/99, 62, 63; 340/568, 608; 436/43, 47, 48; 81/3.2; 53/505, 506; 141/83; 222/52

[56] References Cited
U.S. PATENT DOCUMENTS
4,773,204 12/1988 Rydstrom ............................ 53/506

FOREIGN PATENT DOCUMENTS
0264456 3/1987 European Pat. Off. .
62-6171 1/1987 Japan .
646759 6/1987 Japan .
WO90/08307 7/1990 PCT Int'l Appl. .

Primary Examiner—Robert J. Warden
Assistant Examiner—Laura E. Collins
Attorney, Agent, or Firm—Dana M. Schmidt

[57] ABSTRACT

There is described a stopper detector for use in combination with a stopper remover, so that containers of liquid can be automatically unstoppered in an analyzer if they are in fact stoppered. The stopper detector includes a mechanism for discriminating between a container having a stopper, and an unstoppered container, including one with a cup inserted into the top of the container. It also includes means for generating a signal in response to the discriminating means that is indicative of whether or not a stopper is present, such signal being effective, if present, to activate a following stopper remover.

6 Claims, 3 Drawing Sheets

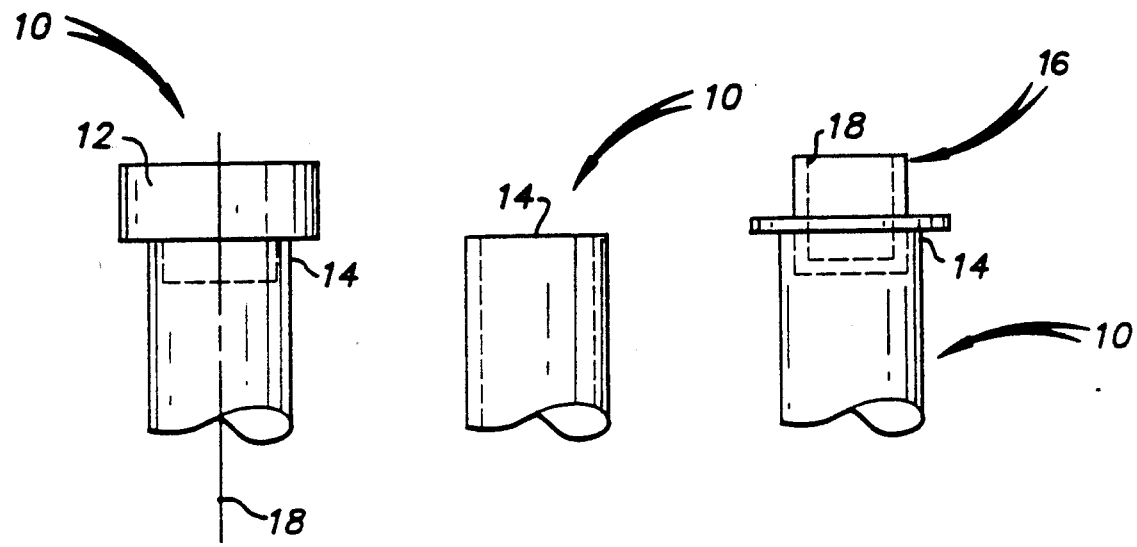
FIG. 1A
STOPPERED
FIG. 1B
UNSTOPPERED
FIG. 1C
CUP AT TOP
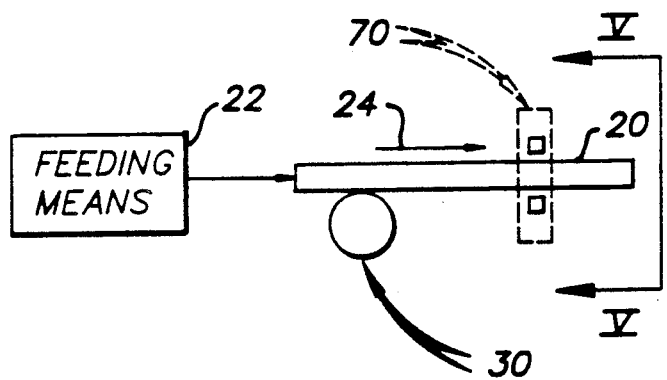
FIG. 2

STOPPER DETECTOR

FIELD OF THE INVENTION

The invention relates to a stopper detector for stoppered containers that, when used with a stopper remover, will automatically activate the latter only if a stopper is present.

BACKGROUND OF THE INVENTION

For liquid analyzers to function, a patient sample needs to be removed, such as by aspiration, from a container. Most preferably, such containers are introduced into an analyzer in a stoppered condition, to protect the sample and the apparatus. Such stoppers then must be removed.

Container-opening devices are well-known in the prior art. Such devices will pull a cork out, as described in EPO Publication No. 264,456; flip up a flip-top cap, as described in Japanese Kokai 64/6759; or pull out a plug, as described in Japanese Kokai 62/6171. In all of these, however, the assumption is made that each container presented in the apparatus has in fact the anticipated cover, presented in the anticipated manner. Unfortunately, that is not always the case. Particularly the absence of a cork cover is unfortunate in the case of a device constructed as in EPO Publication 264,456, since the cork-penetrating prongs are likely to wreak havoc on any metal cover used in place of cork or rubber, or even break the container if an unstoppered container projects up into the path of the prongs.

Although it might be assumed that in the absence of the expected cover, most opening devices will simply proceed harmlessly through their opening motions for a container that has no cover to open, this may not always be the case. With some containers, at least. it is desirable to pour a small fraction of the body liquid into a micro-sample cup that is inserted into the larger container. This cup sits at the top of the container exactly where a cover would be. Most conventional cap-or cover-opening devices would seize or otherwise remove such a cup, thereby not only removing the sample liquid from testing but also dumping its contents into the apparatus.

Therefore, prior to this invention there has been no apparatus or means for automatically detecting whether a stopper is present for removal by stopper-removing means, as compared to no stopper at all or some other device at the top of the liquid-containing tube or container.

SUMMARY OF THE INVENTION

I have constructed apparatus that solves the aforementioned problems.

More specifically, in accord with one aspect of the invention, there is provided in combination, apparatus for removing stopper means for stoppering a liquid-containing tube or container, and detecting means for detecting that stopper means are present. The detecting means comprise means for discriminating between a tube or container having a stopper therein and one that does not, and means responsive to the discriminating means for generating a signal indicative of whether or not a stopper is present, whereby further processing beyond the discriminating means can be prevented or altered in response to the condition of the tube or container at the discriminating means.

In accord with another aspect of the invention, there is provided a mechanical stopper detector useful with apparatus for removing a stopper from a liquid-containing tube or container. The detector comprises means for discriminating by contact with a tube or container, between a contacted tube or container that has a stopper therein, and one that does not, and means responsive to the discriminating means for generating a signal indicative of whether or not a stopper is present, whereby further processing beyond the discriminating means can be prevented or altered in response to the condition of the tube or container at the discriminating means.

Accordingly, it is an advantageous feature of the invention that the apparatus for removing a stopper is first able to automatically detect whether or not a stopper is present to be removed.

It is a related advantageous feature that means are provided for discriminating between a tube or container that is stoppered, and one that is unstoppered or contains a cup in the top that has liquid already tansferred thereto.

Other advantageous features will become apparent upon reference to the detailed description of the embodiments, when read in light of the attached drawings.

DETAILED DESCRIPTION OF THE DRAWINGS

FIGS. 1A-1C are fragmentary elevational views of a tube or container in three possible configurations that can be present;

FIG. 2 is a schematic plan view of apparatus in which both a stopper detector and stopper remover are present;

DESCRIPTION OF THE PREFERRED EMBODIMENT

Figure 3:
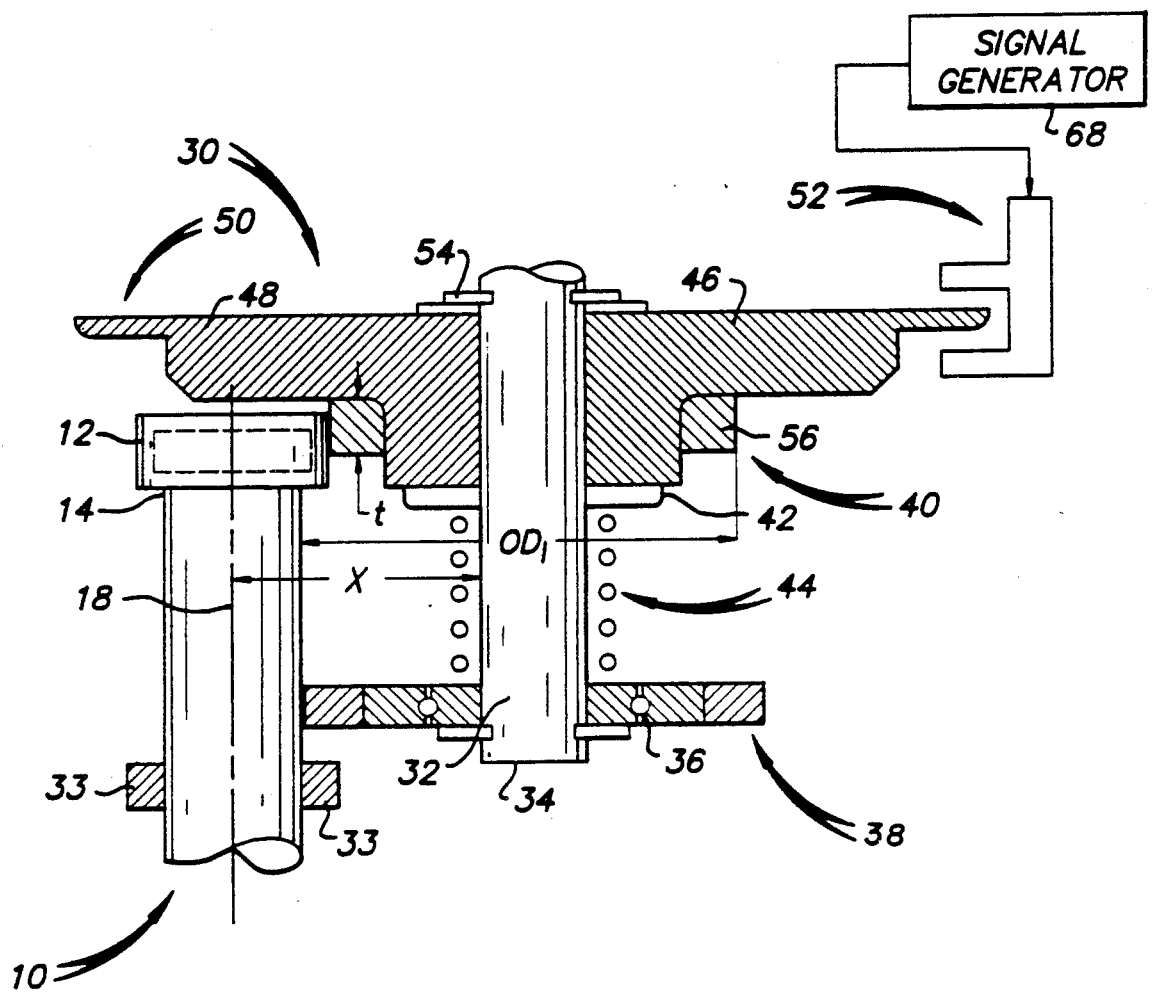
FIG. 3 is a fragmentary elevational view partially in section illustrating the preferred stopper detector of the invention.

The invention is described hereinafter in connection with the preferred embodiments, in which a particular type of stopper detector, namely one that works by mechanical contact, is described for use in an analyzer with a particular type of liquid-containing container and stopper. In addition, the invention is useful regardless of the mechanism by which the apparatus senses the presence or non-presence of a stopper, and regardless of the type of container or stopper used. It is also useful whether the apparatus is part of an analyzer, or not.

FIGS. 1A-1C are illustrative of the problem solved by this invention. A tube or container 10 having an axis 18 is presented to an analyzer (not shown) usually, but not always, with a stopper 12 at the upper end 14, FIG. 1A. As shown container 10 is a 16 mm diameter container, but comparable stoppers and problems exist for other sized containers. In some cases, container 10 is unstoppered so that end 14 is open, FIG. 1B. (Such a situation is usually inadvertent.) More commonly, FIG. 1C, container 10 may be unstoppered, but have loosely sitting at the upper end 14 a micro-sample cup 16 into which patient sample has already been transferred from container 10 (by conventional apparatus, not shown).

Of these configurations, only that of FIG. 1A is intended to have a "stopper" removed. No removal can occur for that of FIG. 1C, since the container to be sampled is the cup 16 that is already unstoppered at its open end 18.

Such containers 10 are preferably presented to a stopper remover 70 by conventional conveyor means 20. Means 20 can be loaded for example by feeding means 22 of any suitable construction or even by hand. The containers are preferably moved along conveyor means 20, arrow 24, in a suitable tray T, FIG. 5. Following stopper removal, liquid is removed from containers 10 and assayed by suitable analyzer apparatus (not shown).

In accordance with the invention, before the containers arrive at stopper remover 70, they pass by stopper detector 30 shown in detail in FIG. 3. Cooperating with detector 30 are container-clamping means 33, that can be constructed to operate similar to the clamping means 134 of stopper remover 70, FIG. 5. To mechanically discriminate by contact between the one stoppered and two unstoppered configurations noted in FIG. 1, detector 30 comprises, FIG. 3, rotating shaft means 32 continuously driven by a motor (not shown). At one end 34 of shaft 32 is anchored a bearing 36. The outer race of bearing 36 is attached to a roller 38 dimensioned to contact a clamped container 10, thus accurately positioning shaft means 32 in the "x" direction from axis 18 of tube 10.

To sense whether or not a stopper is at end 14 of container 10, a disk 40 is freely supported around shaft 32 by a floating washer 42 biased upwardly by a compression spring 44 attached to the inner rotating race of bearing 36. Disk 40 has a shoulder 46 that cooperates with friction member 56 described below, an overhanging portion 48, and a flag portion 50 suitably notched or provided with suitable detectors that are sensed by a conventional optical or magnetic sensor 52. Retaining clip 54 holds disk 40 in place against spring 44.

Figure 4:
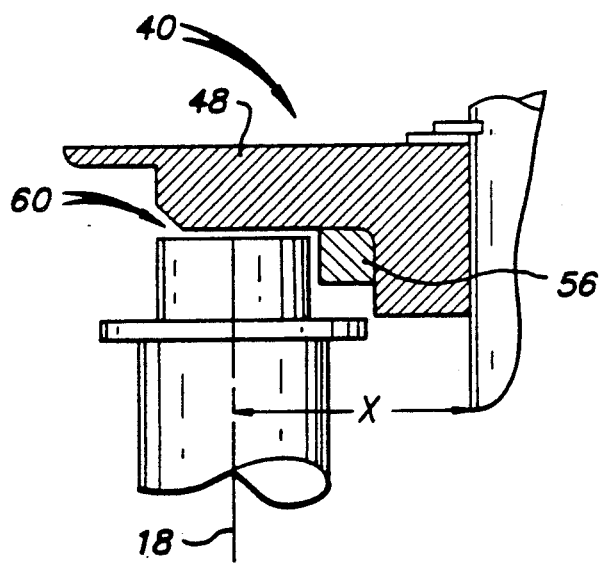
FIG. 4 is a fragmentary elevational view similar to that of FIG. 3, but illustrating the situation when a container is present with a micro-sample cup in place of a stopper.

A frictional member 56 is affixed to shoulder 46, with an outer diameter $OD_1$ that is constructed so as to bear upon a stopper 12, if such is present, but not upon an unstoppered container when dimension "x" is maintained by roller 38. Member 56 thus acts as means for stalling disk 40 when stopper 12 is contacted, which stalling is detected by sensor 52. On the other hand, if only an unstoppered container 10 is present with an open end 14, no contact is made by disk 40 or member 56, and disk 40 continues to rotate. Member 56 can also be provided with a thickness "t" such that, FIG. 4, if a cup 16 is present in place of a stopper, member 56 also refrains from contacting cup 16 while dimension "x" is maintained. (Enough spacing occurs at 60 between cup and disk 40 to keep disk 40 from stalling.) Alternatively, if overhang 48 is intended to hold down cup 16 from vertical bouncing, contact can occur since cup 16 is free to rotate within container 10. In the latter case, member 56 can also contact cup 16 (not shown), since the cup will keep rotating rather than stall out disk 40.

The frictional coupling that occurs between disk 40 and shaft 32 via spring 44 is selected to be sufficient to keep disk 40 rotating with shaft 34, except when member 56 contacts a clamped stopper and stalls out the disk.

Sensor 52 cooperates with a signal-generating means 68, which is conventional, to deliver a signal to stopper remover 70 to actuated it, only if the condition of FIG. 1A exists. If the condition of FIGS. 1B or 1C exists, then no signal is generated by sensor 52 or means 68, and the stopper remover remains inactive.

Figure 5:
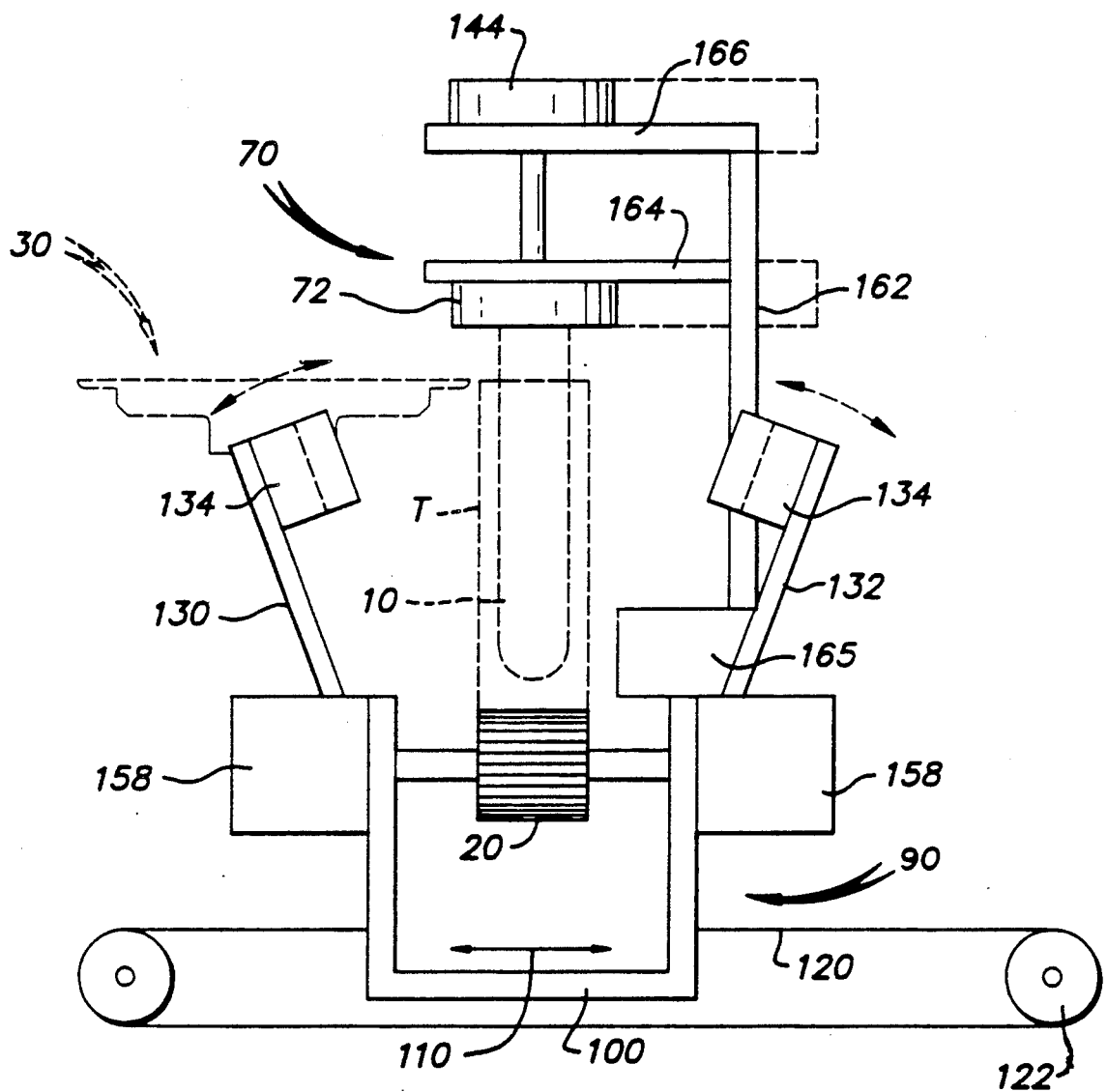
FIG. 5 is a partially schematic elevational view of the stopper remover portion of the apparatus, taken generally along the lin V—V of FIG. 2.

When a container is identified by detector 30 as having a stopper, then stopper remover 70 featuring housing 72 is activated, FIG. 5. Stopper removers are known in the art, for example as shown in Japanese Kokai 62/6171. The stopper remover 70 preferably includes jaws 134 on gripper means 130, 132 mounted at any suitable location, and preferably a location 90 adjacent conveyor means 20. Optionally, conveyor means 20 can be mounted on frame 100 that slides back and forth, arrow 110, on a rail (not shown) as induced by the translation back and forth of a belt 120 driven by pulley 122. Gripper means 130 and 132 are operated by motors 158 also mounted on frame 100. A vertically extending shaft 162 is connected to a rotating motor 165, and supports two platforms 164 and 166. Platform 164 can be used to support housing 72 in a bearing journal (not shown), while platform 166 supports motor 144. Housing 72 contains a suitable gripper (not shown) for engaging stopper 12 of FIG. 1A, and motor 144 is effective to rotate the gripper and stopper until the stopper is removed. Motor 165 serves only to slightly rotate housing 72 and motor 144 out of the way of the other parts, to a location shown in phantom, after a stopper has been removed.

After the stopper is removed from any particular container, the liquid therein can be aspirated and then dispensed onto a test element, by other apparatus of the analyzer, not shown.

Coordination of the stopper remover with the stopper detector and other parts of the apparatus is handled automatically by conventional means, such as a microprocessor, not shown.

The invention has been described in detail with particular reference to preferred embodiments thereof, but it will be understood that variations and modifications can be effected within the spirit and scope of the invention.

What is claimed is:

1. Apparatus for processing liquid patient samples comprising a stopper remover for removing stopper means for stoppering a liquid-containing tube or container, and detecting means for detecting that stopper means are present, said detecting means comprising:

means for discriminating between a tube or container having a stopper therein and one that does not have a stopper, said discriminating means comprising a rotating flag member, means for sensing the rotation of said rotating flag member, means for continuously rotating said flag member adjacent a potentially stoppered tube or container, and means for stopping said rotating flag member in response to the presence of a stopper, and means responsive to said discriminating means for generating a signal indicative of whether a stopper is present, whereby further processing beyond said discriminating means can be prevented or altered in response to the condition of the tube or container at said discriminating means.

2. Apparatus as defined in claim 1, wherein said stopping means comprise a frictional member mounted on said rotating means, said frictional member being fixed with respect to said flag member, and means for positioning said rotating means adjacent a potentially stoppered tube or container a distance effective to contact said frictional member with a stopper but not with an unstoppered tube or container.

3. Apparatus as defined in claim 2, wherein said rotating means include a rotating shaft and biasing means for friction-coupling said frictional member and said flag member to said shaft, and said positioning means comprise a roller freely rotatably mounted on said shaft.

4. A mechanical stopper detector useful with apparatus for removing a stopper from a liquid-containing tube or container, said detector comprising:

means for discriminating by contact with a tube or container, between a contacted tube or container that has a stopper therein and one that does not, said discriminating means comprising a rotating flag member, means for sensing the rotation of said rotating flag member, means for continuously rotating said flag member adjacent a potentially stoppered tube or container, and means for stopping said rotating flag member in response to the presence of a stopper, and means responsive to said discrare placed 5 iminating means for generating a signal indicative of whether or not a stopper is present, whereby further processing beyond said discriminating means can be prevented or altered in response to the condition of the tube or container at said discriminating means.

5. A detector as defined in claim 4, wherein said stopping means comprise a frictional member mounted on said rotating means, said frictional member being fixed with respect to said flag member, and means for positioning said rotating means adjacent a potentially stoppered tube or container a distance effective to contact said frictional member with a stopper but not with an unstoppered tube or container.

6. A detector as defined in claim 5, wherein said rotating means include a rotating shaft and biasing means for friction-coupling said frictional member and said flag member to said shaft, and said positioning means comprise a roller freely rotatably mounted on said shaft.

* * * * *

UNITED STATES PATENT AND TRADEMARK OFFICE
CERTIFICATE OF CORRECTION

PATENT NO. : 5,080,864
DATED : January 14, 1992
INVENTOR(S) : James D. Shaw

It is certified that error appears in the above-indentified patent and that said Letters Patent is hereby corrected as shown below:

Column 6, line 1, should read --and means responsive to said discriminat- --

Signed and Sealed this

First Day of February, 1994

Attest:

BRUCE LEHMAN

Attesting Officer

Commissioner of Patents and Trademarks